US 9,980,666 B2

(12) United States Patent
Bresch et al.

(10) Patent No.: US 9,980,666 B2
(45) Date of Patent: May 29, 2018

(54) SYSTEM AND METHOD FOR DETERMINING A VITAL SIGN OF A SUBJECT

(71) Applicant: KONINKLIJKE PHILIPS N.V., Eindhoven (NL)

(72) Inventors: Erik Bresch, Eindhoven (NL); Jens Muehlsteff, Aachen (DE)

(73) Assignee: KONINKLIJKE PHILIPS N. V., Eindhoven (NL)

( * ) Notice: Subject to any disclaimer, the term of this patent is extended or adjusted under 35 U.S.C. 154(b) by 836 days.

(21) Appl. No.: 14/173,117

(22) Filed: Feb. 5, 2014

(65) Prior Publication Data

US 2014/0235976 A1 Aug. 21, 2014

Related U.S. Application Data

(60) Provisional application No. 61/765,096, filed on Feb. 15, 2013.

(30) Foreign Application Priority Data

Feb. 15, 2013 (EP) .................................. 13155430

(51) Int. Cl.
*A61B 5/1455* (2006.01)
*A61B 5/00* (2006.01)
(Continued)

(52) U.S. Cl.
CPC ........ *A61B 5/14551* (2013.01); *A61B 5/0002* (2013.01); *A61B 5/02416* (2013.01);
(Continued)

(58) Field of Classification Search
CPC ............ A61B 5/14551; A61B 5/14552; A61B 5/6826; A61B 5/6838; A61B 5/1495
See application file for complete search history.

(56) References Cited

U.S. PATENT DOCUMENTS

| | | | | |
|---|---|---|---|---|
| 5,025,791 A | * | 6/1991 | Niwa ................. | A61B 5/14552 600/324 |
| 5,490,523 A | * | 2/1996 | Isaacson ............ | A61B 5/02427 600/323 |

(Continued)

FOREIGN PATENT DOCUMENTS

| | | |
|---|---|---|
| JP | 11155823 | 6/1999 |
| JP | 2009-247733 | 10/2009 |

(Continued)

OTHER PUBLICATIONS

Borowski, M., et al.; Medical device alarms; 2011; Biomed Tech; 56:73-83.

(Continued)

*Primary Examiner* — Eric Winakur

(57) ABSTRACT

A system for determining a vital sign of a subject releases the likelihood of generating and outputting false alarms. The system includes a vital sign processor that processes the vital sign information signal measured by a sensor attached to a subject to obtain a vital sign of said subject. An image analysis unit detects motion of a marker attached to the sensor from image data obtained by an imaging unit from at least an imaging region containing the sensor. An alarm unit generates and outputs an alarm signal based (1) on the measured vital sign information signal and/or the obtained vital sign and (2) the detected motion of said marker.

20 Claims, 4 Drawing Sheets

(51) Int. Cl.
*A61B 5/024* (2006.01)
*A61B 5/11* (2006.01)

(52) U.S. Cl.
CPC .......... *A61B 5/1127* (2013.01); *A61B 5/7221* (2013.01); *A61B 5/746* (2013.01)

(56) References Cited

U.S. PATENT DOCUMENTS

| | | | |
|---|---|---|---|
| 6,300,974 B1 * | 10/2001 | Viala | G01V 8/10 348/61 |
| 6,684,090 B2 * | 1/2004 | Ali | A61B 5/1455 600/323 |
| 6,721,585 B1 * | 4/2004 | Parker | A61B 5/14552 600/310 |
| 6,724,930 B1 * | 4/2004 | Kosaka | G01B 11/002 382/154 |
| 7,444,178 B2 | 10/2008 | Goldbach | |
| 7,809,194 B2 | 10/2010 | Zhang et al. | |
| 7,890,153 B2 * | 2/2011 | Hoarau | A61B 5/14551 600/323 |
| 8,577,434 B2 * | 11/2013 | Merchant | A61B 5/14552 600/310 |
| 8,577,439 B2 | 11/2013 | Pinter | |
| 8,821,418 B2 | 9/2014 | Meger | |
| 9,386,923 B2 | 7/2016 | Winter | |
| 2001/0024512 A1 | 9/2001 | Yoronka et al. | |
| 2002/0103423 A1 * | 8/2002 | Chin | A61B 5/14552 600/322 |
| 2003/0063292 A1 * | 4/2003 | Mostafavi | A61B 6/463 356/614 |
| 2003/0139656 A1 * | 7/2003 | Kiani | A61B 5/6843 600/322 |
| 2007/0076935 A1 * | 4/2007 | Jeung | A61B 5/08 382/128 |
| 2007/0132597 A1 | 6/2007 | Rodgers | |
| 2008/0183058 A1 * | 7/2008 | Mannheimer | A61B 5/02455 600/323 |
| 2008/0221399 A1 | 9/2008 | Zhou et al. | |
| 2009/0068620 A1 | 3/2009 | Knobel et al. | |
| 2010/0327063 A1 * | 12/2010 | Medina | A61B 5/14552 235/454 |
| 2011/0060537 A1 | 3/2011 | Moodie | |
| 2011/0130655 A1 * | 6/2011 | Nielson | A61N 5/1049 600/426 |
| 2012/0016245 A1 | 1/2012 | Niwa et al. | |
| 2012/0029317 A1 | 2/2012 | Doyle et al. | |
| 2012/0253142 A1 | 10/2012 | Meger | |
| 2015/0105670 A1 | 4/2015 | Bresch | |

FOREIGN PATENT DOCUMENTS

| | | |
|---|---|---|
| WO | 2004023783 A2 | 3/2004 |
| WO | 2005044378 A1 | 5/2005 |
| WO | 2008055949 A1 | 5/2008 |

OTHER PUBLICATIONS

Verkruysse, W., et al.; Remote plethysmographic imaging using ambient light; 2008; Opt. Express; 16(26) 21434-21445.

* cited by examiner

SYSTEM AND METHOD FOR DETERMINING A VITAL SIGN OF A SUBJECT

CROSS REFERENCE TO RELATED APPLICATIONS

This application claims the benefit of U.S. provisional application Ser. No. 61/765,096 filed Feb. 15, 2013 and European provisional application serial no. 13155430.5 filed Feb. 15, 2013, both of which are incorporated herein by reference.

FIELD OF THE INVENTION

The present invention relates a system and method for determining a vital sign of a subject and to a sensor for use in such a system and method. The present invention particularly relates to patient monitoring systems and methods, e.g. as used in intensive care units in hospitals.

BACKGROUND OF THE INVENTION

Vital signs of a person, for example heart rate (HR), respiration rate (RR) or oxygen saturation (i.e. SpO2), serve as indicators of the current state of a subject (i.e. a person or animal) and as powerful predictors of serious medical events. For this reason, vital signs are monitored in inpatient and outpatient care settings, at home or in further health, leisure and fitness settings. Various sensors can thus be used to measure a vital sign information signal from which a corresponding vital sign can be obtained.

One way of measuring vital signs is plethysmography. Plethysmography typically refers to the measurement of volume changes of an organ or a body part and in particular to the detection of volume changes due to a cardio-vascular pulse wave traveling through the body of a subject with every heart beat. Photo-plethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise further embedded information attributable to respiration and further physiological phenomena. By evaluating the transmissivity and/or reflectivity at different wavelengths (typically red and infrared), the blood oxygen saturation can be determined.

Conventional pulse oximeters for measuring the heart rate and the oxygen saturation of a subject are attached to the skin of the subject, for instance to a finger tip, earlobe or forehead. Therefore, they are referred to as 'contact' PPG devices. A typical pulse oximeter comprises a red and an infrared LED as light sources and a photodiode for detecting light that has been transmitted through patient tissue. The transmissivity in the red and infrared spectral range is measured by time multiplex. The transmissivity over time gives the red and infrared PPG waveforms.

It is well known that the frequent occurrence of false medical alarms in the hospital, e.g., alarms generated by patient monitoring devices in the intensive care unit (ICU), presents a serious and unresolved problem because it leads to a desensitization of the caregivers against alarms. Furthermore, it is known that the high sensitivity of modern patient monitoring systems leads to alarm noise levels around 80 dB in today's average ICUs, which is comparable to the traffic noise on a main street. However, up to 90% of the registered alarms are medically irrelevant. The technical alarms, which make up about 22% of all alarms, are often due to bad sensor signals due to patient motion. This is especially the case for SpO2-related alarms, which make up 79% of the technical alarms.

It appears therefore beneficial to obtain relevant information on the sensor's motion and to utilize this information to reduce the false alarm probability. This is particularly important in conjunction with "cable-less patient" approaches, where the patient can move around freely in the hospital.

SUMMARY OF THE INVENTION

It is an object of the present invention to provide an improved system and method for determining a vital signs of a subject by which the false alarm probability is reliably and considerably reduced. It is another object of the present invention to provide a sensor for use in such a system and method.

In a first aspect of the present invention a system for determining a vital sign of a subject is presented that comprises
a vital sign processor that processes said vital sign information signal measured by a sensor attached to a subject to obtain a vital sign of said subject,
an image analysis unit that detects motion of a marker attached to said sensor from image data obtained by an imaging unit from at least an imaging region containing said sensor, and
an alarm unit that generates and outputs an alarm signal based on the measured vital sign information signal and/or obtained vital sign and on the detected motion of said marker In a further aspect of the present invention a method for determining a vital sign of a subject is presented that comprises
processing a measured vital sign information signal of said subject,
detecting motion of a marker attached to said sensor from image data obtained from at least an imaging region containing said sensor, and
generating and outputting an alarm signal based on the measured vital sign information signal and/or obtained vital sign and on the detected motion of said marker.

In yet another aspect of the present invention, there is provided a computer program which comprises program code means for causing a computer to perform the steps of the proposed method when said computer program is carried out on a computer. Further, a non-transitory computer-readable recording medium that stores therein such a computer program product, which, when executed by a processor, causes said steps of the method disclosed herein to be performed, is presented.

Preferred embodiments of the invention are defined in the dependent claims. It shall be understood that the claimed method, computer program and medium have similar and/or identical preferred embodiments as the claimed system and as defined in the dependent claims.

The use of video cameras for patient monitoring, particularly in the hospital, becomes more and more widespread. Hereby, the image data (e.g. continuous video data) can be used to directly (unobtrusively and without contact) measure vital sign information using the principle of remote photoplethysmography (remote PPG, as e.g. described in Wim Verkruysse, Lars O. Svaasand, and J. Stuart Nelson, "Remote plethysmographic imaging using ambient light", Optics Express, Vol. 16, No. 26, December 2008) or to obtain more general non-vital sign information on the patient state such as through video actigraphy. In the latter case, a video analysis may reveal some global information in the patient's movements, but it may be insufficient information to make judgments on the reliability of particular sensor signals coming from the patient.

The present invention therefore proposes the integration of a marker with the (medical) sensor. By use of the—often already available imaging unit (e.g. of a remote PPG system or a video actigraphy system)—image data of a certain imaging region, in which the sensor is located are obtained so that movements of the sensor can be reliably and accurately determined from the detected motion of the marker identified in the image data. Thus, a real-time analysis of the motion trajectories of the marker can be made from the image data that provides direct evidence on the sensor's motion and signal reliability. This evidence can then be used by the alarm unit to reduce the false alarm probability.

According to an embodiment said alarm unit is configured to generate and output an alarm signal if the measured vital sign information signal and/or obtained vital sign fulfills a first condition and if the detected motion of said marker fulfills a second condition. These conditions are generally predetermined and dependent on or more of the following factors including the kind of sensor, the kind of marker, the position of attachment of the sensor to the subject's body, the desired accuracy of the false alarm suppression, etc. For instance, for a SpO2 sensor generally a different first condition is used than for a heart rate sensor. The conditions may also be available for modification by the user.

According to another embodiment said alarm unit is configured to generate and output an alarm signal if the measured vital sign information signal and/or obtained vital sign fulfills a first condition, wherein said first condition is adapted based on the detected motion of said marker. Thus, for instance, if the marker is moving stronger, the first condition is adapted such that false alarms are suppressed or that an alarm is only generated and outputted if a higher likelihood is given that an alarm really exists.

According to another embodiment said alarm unit is configured to generate an alarm signal if the measured vital sign information signal and/or obtained vital sign fulfills a first condition, wherein the output of said alarm signal is suppressed if the detected motion of said marker fulfills a second condition. Thus, another way of controlling the generation and output of alarms is provided according to this embodiment.

The alarm unit is preferably configured to use as first condition a lower and/or upper threshold of the level of the measured vital sign information signal and/or obtained vital sign. For instance, an upper and/or lower heart rate limit or a lower oxygen saturation limit may be used if a corresponding sensor is used.

Still further, the alarm unit is preferably configured to use as second condition a motion threshold indicating the intensity, frequency and/or pattern of the motion of said marker. Thus, for instance dependent on the kind and location of sensor an appropriate condition may be selected.

Advantageously, the alarm unit comprises a communication interface for communicating said alarm signal to an alarm indication unit for indicating an alarm. While the alarm unit may directly output the alarm, e.g. as visual and/or audible signal, it is preferred that the alarm is indicated on a separate indication unit. This indication unit may be in the form of a display, a loudspeaker, a mobile phone, etc. on which the alarm is issued, e.g. as blinking signal, loud alarm sound or phone call. Various other embodiments exist for such an indication unit, which may be arranged at a remote location, e.g. at a central monitoring room or nurse room at a station of a hospital.

There are various embodiments of markers that can be used according to the present invention. In a first embodiment the marker is a passive marker comprising a graphical pattern. Said graphical pattern is preferably designed such that motion of the marker can be detected from said image data as good as possible. Further, in an embodiment the graphical pattern is preferably machine-readable (such as a QR-code, a bar code or simply graphical signs or letters), in particular if the graphical pattern is configured to contain information about the subject and/or the sensor and wherein said image analysis unit is configured to determine said information from said graphical pattern, as proposed in a further embodiment. The marker can then be tracked with the imaging unit. Such a machine-readable marker can also be retro-fitted to existing sensors. For example, the marker can be deployed as a sticker which can be put on an existing SpO2 contact finger probe, or a blood pressure cuff, etc.

In a second embodiment the marker is an active marker configured to emit light. For instance, an active light source (e.g. an LED) can be used, or a self-illuminating material (e.g. fluorescent or phosphorescent material) can be used in or on the marker. The active marker can be thought of as a light beacon, which emits light into the environment. The intensity of the light can be time varying, i.e., coded light can be emitted. With coded light, information about the particular sensor and/or the patient can be broadcast, e.g., each sensor may emit its own unique signature light code as proposed in a preferred embodiment according to which the active marker is configured to emit light containing information about the subject and/or the sensor and wherein said image analysis unit is configured to determine said information from said emitted light. The emitted light may be visible or invisible (e.g. infrared light) to the human eye. By means of the emitted light signature a sensor can then be uniquely identified and tracked by the imaging unit.

In a third embodiment the marker may both comprise an active and a passive marker element as described above.

Preferably, said image analysis unit is configured to detect the location of said marker and one or more additional markers attached to one or more further sensors and/or to the subject's body from said image data. Further, said alarm unit is configured to generate and output an alarm signal if it is detected that a sensor is not attached or attached incorrectly or to a wrong portion of the subject's body and/or is attached to a wrong subject. Thus, by use of several markers several sensors and subjects can be easily distinguished, and also certain situations of wrong use or malfunction of a sensor can be detected.

Still further, in an embodiment said alarm unit is configured to generate and output an alarm signal if the marker cannot be detected in said imaging region. This enables the detection of situations when a sensor is covered, e.g. by a blanket, or fell off from the patient, or even a situation when a patient is no longer in the imaging region at all, e.g. fell off from the bed.

It shall be noted that the term 'vital sign' as used in the context of the present invention refers to a physiological parameter of a subject. In particular, the term 'vital sign' comprises the heart rate (HR), the heart rate variability, Traube Hering Mayer waves, the respiratory rate (RR), body temperature, blood pressure, the concentration of a substance in blood and/or tissue, such as an oxygen saturation or a glucose level. A 'sensor' as used here is thus a sensor that can measure one or more vital sign information signal from which such a vital sign can be obtained, i.e. either directly represents a vital sign or can be processed or analyzed to obtain the vital sign.

Still further, it shall be noted that the sensor(s) for sensing vital sign information signal(s) and the imaging unit for obtaining image data of at least an imaging region containing said sensor are generally no essential parts of the proposed system. In preferred embodiments, however, the sensor(s) and/or the imaging unit are part of the proposed system.

In a preferred embodiment the sensor is a plethysmographic sensor comprising at least one light source for emitting light onto skin covered by said sensor, wherein said sensor is designed such that light from at least one light source is emitted in a direction away from the skin so that said light source functions as active marker. Thus, it is proposed to reuse one or more light sources (e.g. LEDs, for instance an invisible infrared LED), which are already integrated in the sensor, along with its existing wiring to facilitate the light beacon functionality.

Preferably, in an embodiment at least part of the sensor housing that carries the one or more light sources is made from a translucent material. This ensures that the sensor can be seen from many (preferably all) directions, i.e. the detection of the light source (as marker) is not (much) dependent on the actual position of the subject's hand. As an additional effect, the large surface of the sensor works as a light emitter and achieves a closer to 360 degrees emission pattern.

Still further, the electrical current or voltage for driving said light source is configured such that it is it modulated at a frequency that is higher than the heart rate of the subject. Thus, high-frequency coded light emission is achieved at no additional hardware cost in the sensor or in the wiring. Hereby, the light modulation does not interfere with the SpO2 measurement process as long as the light modulation is in a high frequency band compared with the heart rate (say above 30 Hz). The SpO2 measurement and coded light emission could also be done sequentially in a fast time-division multiplex fashion.

In still another aspect of the present invention a plethysmographic sensor is presented sensor comprising at least one light source for emitting light onto a subject's skin covered by said sensor and a light detector for receiving light reflected from and/or transmitted through the subject's skin, wherein said sensor is designed such that light from at least one light source is emitted in a direction away from the skin.

Finally, in still another aspect of the present invention a system for determining a vital sign of a subject is presented comprising
a plethysmographic sensor comprising at least one light source that emits light onto a subject's skin covered by said sensor and a light detector that receives light reflected from and/or transmitted through the subject's skin, wherein said sensor is designed such that light from at least one light source is emitted in a direction away from the skin,
a vital sign processor that processes said vital sign information signal measured by said sensor,
an image analysis unit that detects motion of said sensor from image data obtained by an imaging unit from at least an imaging region containing said sensor, and
an alarm unit that generates and outputs an alarm signal based on the measured vital sign information signal and/or obtained vital sign and on the detected motion of said sensor.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
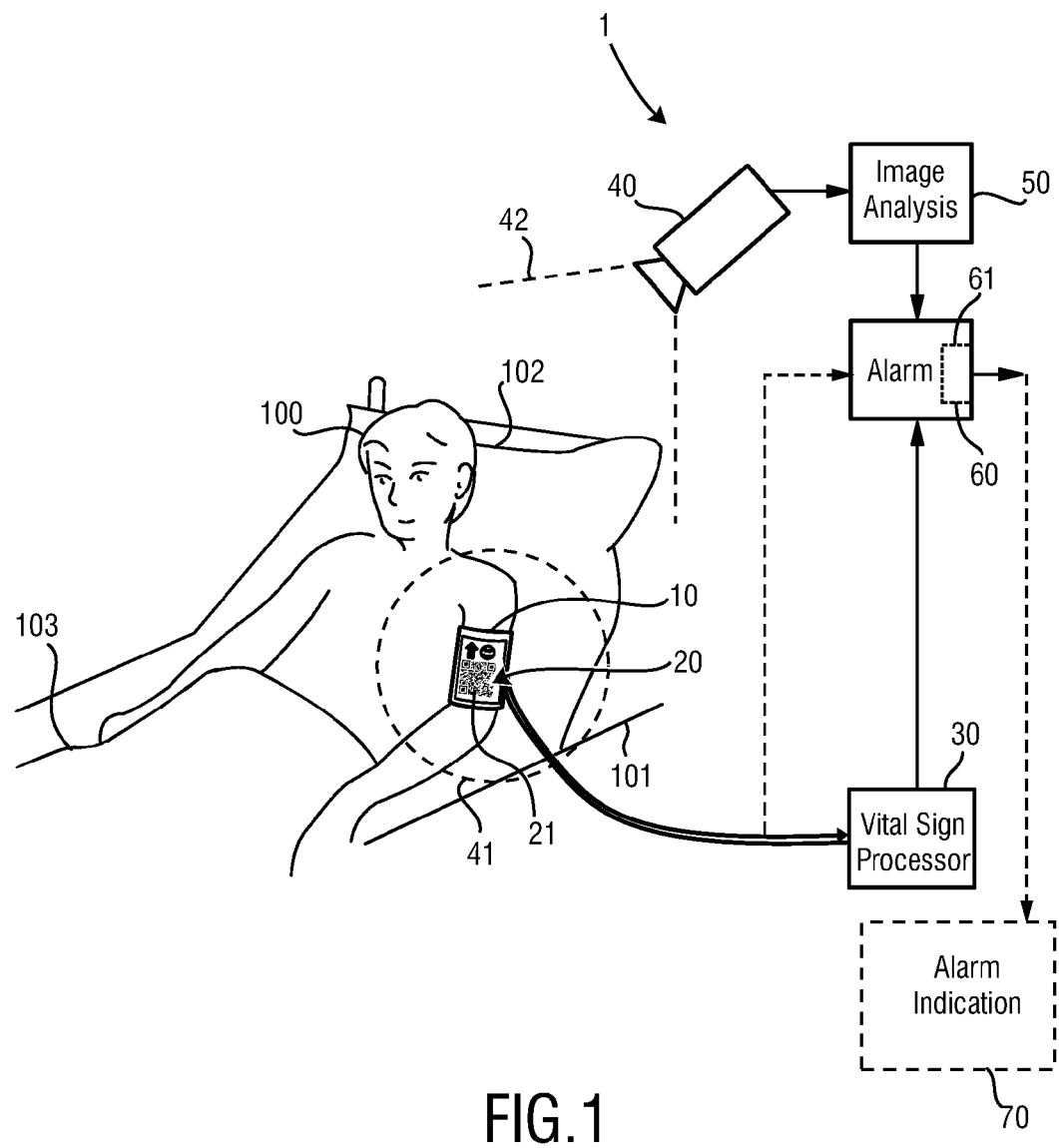
FIG. 1 shows a first embodiment of a system for determining a vital sign of a subject.

FIG. 1 schematically shows a first embodiment of a system 1 for determining a vital sign of a subject 100. The subject 100, in this example a patient, lies in a bed 101, wherein the head of the subject 100 is located on a pillow 102 and the subject 100 is covered with a blanket 103. A sensor 10 is fixed to the subject 100 for measuring a vital sign information signal of said subject. Here, the sensor 10 is a blood pressure cuff arranged on the subject's upper are for measuring the blood pressure of the subject 100.

A marker 20 is attached to the sensor 10, e.g. printed on the outer surface of the blood pressure cuff or attached there in the form of a sticker. In this embodiment the marker 20 is a passive marker comprising a graphical pattern 21, here a so-called QR-code. The QR-code may feature different structural elements allowing for a machine-readable determination of the orientation and/or location of the graphical pattern 21. The marker 20 may be visible or invisible to the human eye, e.g. printed by use of a certain (e.g. infrared or fluorescent) ink so that it can only be detected by use of a special imaging unit and/or after illumination with a certain light source (e.g. with infrared light).

The system 1 comprises a vital sign processor 30 for processing the vital sign information signal measured by the sensor 10 to obtain a vital sign of said subject, i.e. to obtain the blood pressure (in particular the systolic and the diastolic pressure) for which the signal output by the sensor 10 may need to be processed or may already contain this information, i.e. the vital sign information signal may directly represent the vital sign or may need some processing to obtain the vital sign.

An imaging unit 40 is provided for obtaining image data of at least an imaging region 41 containing said sensor 20. Said imaging unit 40 is preferably a camera, such as a video camera (e.g. a CCD camera or an infrared camera), having a field of view 42 that is directed to the desired imaging region in which the sensor 20 is located. Preferably, the field of view 42 is configured to monitor a larger area, e.g. an area containing the complete subject 100. In certain practical situations, such as in an ICU of a hospital, such an imaging unit 40 is already available, e.g. for monitoring the subject 100 or for unobtrusively determining a vital sign using the principle of remote photo-plethysmography.

If a special marker is used which requires a certain illumination to be detectable by the imaging unit 40, e.g. requires illumination by infrared light, a corresponding illumination unit (e.g. an infrared LED) may be provided in addition (not shown in FIG. 1).

The system 1 further comprises an image analysis unit 50 for detecting motion of a marker 20 attached to said sensor 10 from said image data obtained by said imaging unit 40. Said image analysis unit 50 may be an image processor, e.g. using an objection detection or image recognition algorithm, that is adapted to detect the location and/or orientation of the marker 20 in the image data and that is able to detect motion of the marker 20 at a high accuracy. For instance a motion trajectory, i.e. motion over time, of the marker 20 can be detected which reflects motion of the sensor 10 over time.

Finally, the system 1 comprises an alarm unit 60 for generating and outputting an alarm signal based on the measured vital sign information signal and/or obtained vital sign and on the detected motion of said marker 20. The alarm unit 60 may be a processor for processing said signals to determine if an alarm shall be generated and outputted or not.

Generally, an alarm is generated if the vital sign information signal and/or the vital sign fulfill a predetermined first condition, which may be predetermined by the user or a monitoring person (e.g. a nurse or a physician). In the example of blood pressure as vital sign, the first condition may be a lower and/or an upper limit value for the systolic and/or the diastolic blood pressure, wherein the limit values generally depend on the patient and his health condition. For instance, if a predetermined upper limit value for the systolic blood pressure is exceeded an alarm shall be generated and outputted to inform the monitoring person (e.g. via a signal on an alarm indicator, such as a display in a central monitoring room) that said person needs particular attention, e.g. administration of a certain medicament or a medical treatment.

In practical situations the vital sign information signal measured by the sensor 10 may be falsified or bad for various reasons. One main reason are movements of the subject 100 which can generally not be prevented. Such movements may not be very critical for blood pressure measurements, but are quite critical for SpO2 measurements where they often lead to false alarms in practice.

According to the present invention the number of false alarms is considerably reduced with high reliability, whereby real alarms are not suppressed. This is achieved by additionally taking the detected motion of the marker 20 and, thus, of the sensor 10 into account by the alarm unit 60. In general, if the sensor 10 moved too much during the measurement of a vital sign information signal which would result in an alarm, the alarm is either considered as a false alarm, or further measurements are taken to get a measurement without (or with less) sensor movement, or the first condition is adapted to make sure that there is really a condition for generating and outputting a 'real' alarm and not a situation where the movement falsified the measurement such that it looks like in a real alarm situation.

In particular, in one embodiment the alarm unit 60 generates and outputs an alarm signal if the measured vital sign information signal and/or obtained vital sign fulfills a first condition and if the detected motion of said marker 20 fulfills a second condition. Generally, said first condition may be a lower and/or upper threshold of the level of the measured vital sign information signal and/or obtained vital sign (in the above example an upper level of the systolic blood pressure). The second condition may be a motion threshold indicating the intensity, frequency and/or pattern of the motion of said marker. Thus, if the marker has been moved less than 'allowed' by said second condition (i.e. with only little intensity or even not at all) an alarm is generated and outputted if the first condition is met, otherwise an alarm is not generated and/or outputted even if the first condition is met.

In another embodiment the alarm unit 60 generates and outputs an alarm signal if the measured vital sign information signal and/or obtained vital sign fulfills a first condition, wherein said first condition is adapted based on the detected motion of said marker. For instance, if motion of the marker is detected, in the above example the upper level of the systolic blood pressure may be increased which must be achieved to judge the blood pressure measurement as critical justifying the generation and output of an alarm.

In still another embodiment the alarm unit 60 generates and outputs an alarm signal if the measured vital sign information signal and/or obtained vital sign fulfills a first condition, wherein the output of said alarm signal is suppressed if the detected motion of said marker fulfills a second condition. For instance, if the marker has been moved more than 'allowed' by said second condition an alarm is not outputted even if the first condition is met.

The output of the alarm by the alarm unit 60 shall be understood such that at least a signal is outputted that indicates that an alarm has been generated and shall be signaled in an appropriate way. Thus, the signal output of the alarm unit 60 is at least a kind of control signal that controls another (possibly remote) entity 70, e.g. a display, loudspeaker, pager or mobile phone) to indicate an alarm, e.g. show a blinking signal assigned to an icon representing a particular room or patient. For this purpose the alarm unit 60 optionally comprises a communication interface 61 for communicating said alarm signal (e.g. via a (wired or wireless) computer network connection, a telephone network, mobile phone network, etc.) to an alarm indication unit 70 (said another entity) for indicating the alarm.

Figure 2:
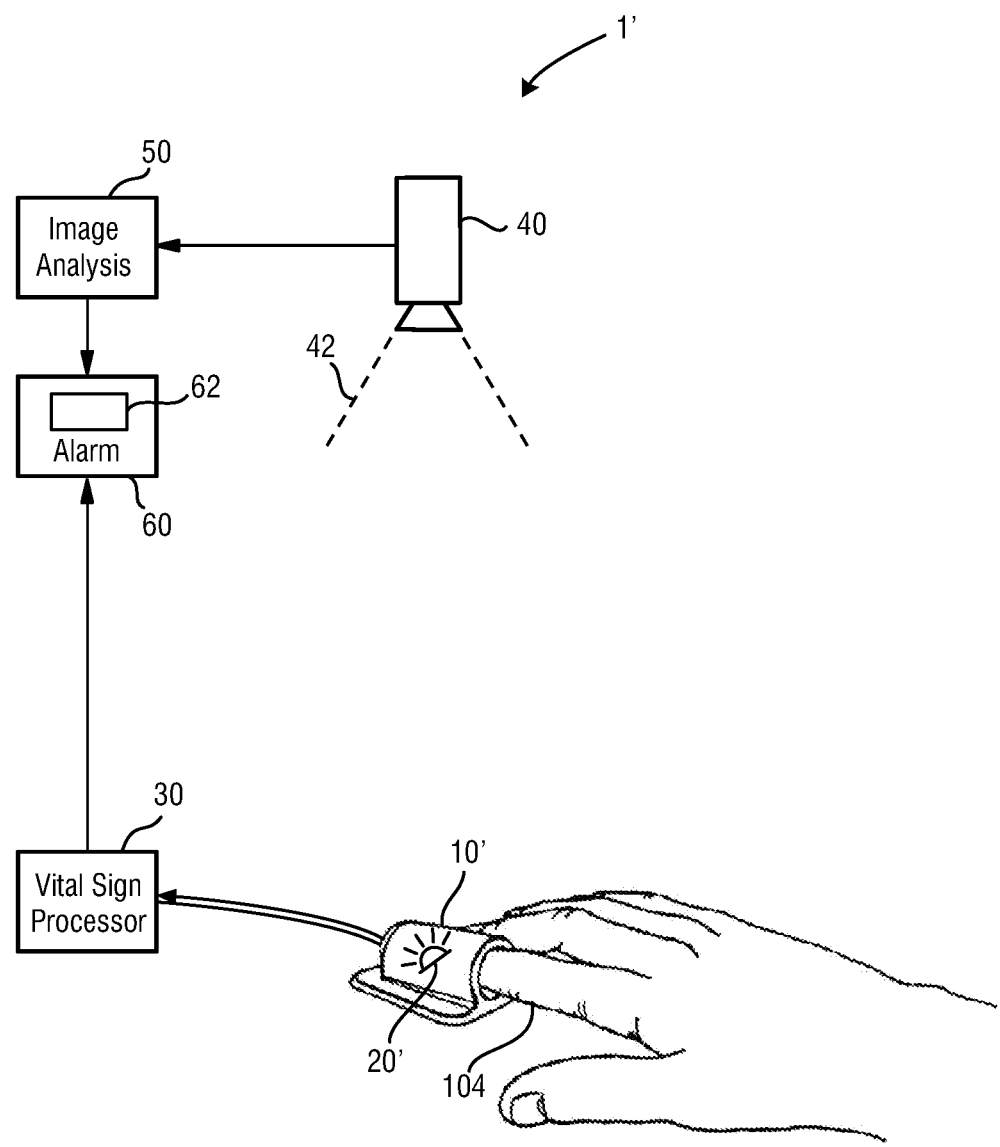
FIG. 2 shows a second embodiment of a system for determining a vital sign of a subject.

FIG. 2 schematically shows a second embodiment of a system 1' for determining a vital sign of a subject 100. In this embodiment a pulse oximeter in the form of a fingerclip is used as sensor 10', which is arranged at a patient's finger 104 for continuously measuring the oxygen saturation (SpO2) as vital sign. Such pulse oximeters are generally known in the art and shall not be described herein in more detail.

In or on the sensor 10' an active marker 20' is arranged, here in form of a light source, e.g. an LED emitting visible or infrared light. Within the image data the imaging unit 40 can detect the active marker 20' and can detect movements of the active marker 20' (and, thus, of the sensor 10') over time. The other elements of the system basically correspond to the corresponding elements of the system 1 shown in FIG. 1.

The marker 20' can be thought of as a light beacon, which emits light into the environment. The intensity of the light can be time varying, i.e., coded light can be emitted. With coded light, information about the particular sensor 20' and/or the subject 100 can be broadcast. In case of using several sensors each provided with its individual marker each marker preferably emits its own unique signature light code. By means of the emitted light signature a sensor can then be uniquely identified and tracked with the imaging unit 40, e.g. a video camera system. The real-time analysis of the motion trajectories of the light beacon from the image data provides direct evidence on the sensor's motion and signal reliability. This evidence can then be used in alarm unit to reduce the false alarm probability as explained above.

Further, in this embodiment the alarm unit 60 comprises an alarm indication unit 62, e.g. a display and/or a loudspeaker, for directly outputting an alarm, e.g. in the form of an audiovisual signal.

Conventional plethysmographic sensors have a light source built in. For example, SpO2 contact sensors (such as a finger clip sensor or an ear clip sensor) have a red LED and an infrared LED which shine light through the attached body part and a photo detector for receiving light reflected from and/or transmitted through tissue. The housing of such sensors is generally made of non-translucent material to optically shield the photo detector from other (interfering) light sources that might be present in the environment.

Figure 5:
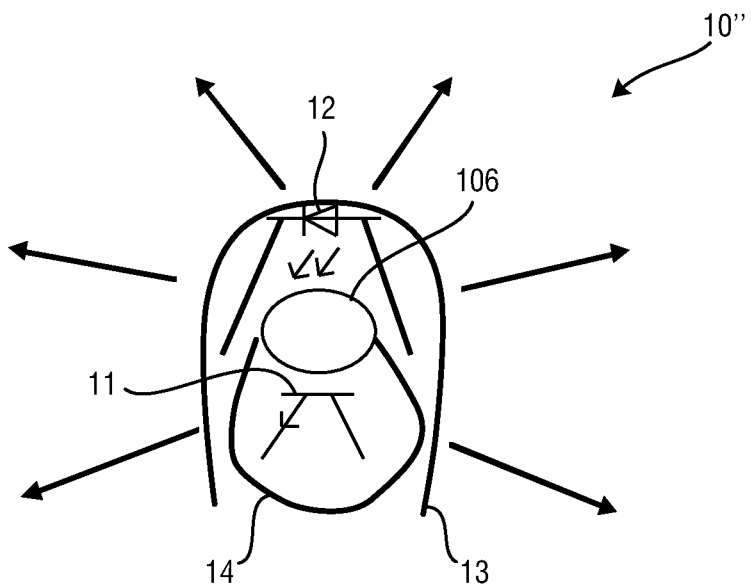
FIG. 5 shows another embodiment of a sensor for use in a system according to the present invention.

In a further embodiment of a sensor 10" shown in FIG. 5 used in an embodiment of the system according to the present invention such a sensor is used but with a sensor housing designed such that the light from one of the light sources (preferably the invisible IR light source) is also emitted into the environment, i.e. in a direction away from the skin. The cross section of an embodiment of such a sensor 10" depicted in FIG. 5 (designed as finger clip sensor or SpO2 sensor) shows an optically isolated photo detector 11, an LED light source 12, a translucent outer part 13 of the housing and an opaque inner part 14 (as optical shield around part of the photo detector 11) of the housing. In the middle between the photo detector 11 and the LED light source 12 the tissue 106 (i.e. the finger) is arranged. Any cabling is not shown, since it is equivalent to that of a conventional SpO2 sensor.

Should the LED light source 12 itself allow too much stray light to pass from the environment into tissue 106 then two optically separated LEDs (not shown) can be used in another embodiment (but electrically connected in parallel, i.e. with no additional wiring). One LED light source then illuminates the tissue 106 (downwards in FIG. 5) and the other LED light source then illuminates (upwards in FIG. 5) the translucent part 13 of the sensor housing.

Thus, rather than using an additional light source that functions as marker 20' as shown in FIG. 2, one of the already available light source(s) is used as active marker allowing detection of movements of the sensor 10" as explained above.

An embodiment of a system for determining a vital sign of a subject comprising such a sensor 10" may thus be configured to comprise a plethysmographic sensor comprising at least one light source that emits light onto a subject's skin covered by said sensor and a light detector that receives light reflected from and/or transmitted through the subject's skin, wherein said sensor is designed such that light from at least one light source is emitted in a direction away from the skin, a vital sign processor that processes said vital sign information signal measured by said sensor, an image analysis unit that detects motion of said sensor from image data obtained by an imaging unit from at least an imaging region containing said sensor, and an alarm unit that generates and outputs an alarm signal based on the measured vital sign information signal and/or obtained vital sign and on the detected motion of said sensor.

Furthermore, in still another improvement the electrical current or voltage supplied to the light source 20' (in FIG. 2) or 12 (in FIG. 5) is modulated with a high frequency information signal for light-code generation. This high frequency modulation has no effect on the actual SpO2 measurement process if the high frequency is well above the heart rate.

Thus, without any additional wiring, hardware or circuitry in the sensor, it be can easily transformed into a light beacon which emits coded light. This can then be used for false alarm suppression as described above. Further, such embodiments of sensors ensure that the light source acting as light beacon is visible (as much as possible) from any direction and under any position in which the patient might hold his hand. Preferably, in such an embodiment the light source emits the (preferably coded) light in an all-around (360 degrees) pattern.

Figure 3:
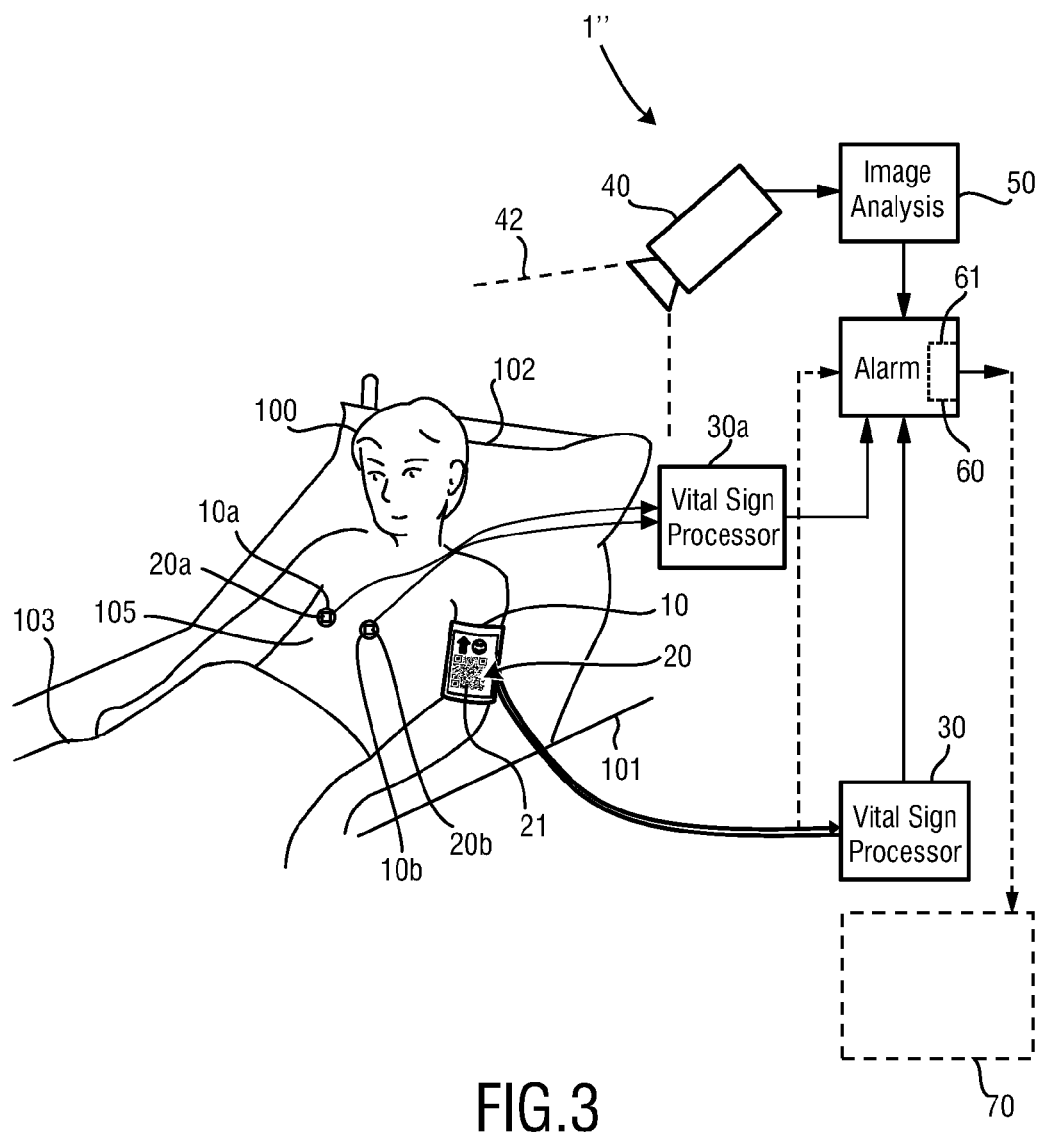
FIG. 3 shows a third embodiment of a system for determining a vital sign of a subject.

FIG. 3 schematically shows a third embodiment of a system 1" for determining a vital sign of a subject 100. In this embodiment the system 1" comprises, in addition to the elements of the system 1 shown in FIG. 1, additional sensors 10*a*, 10*b* which are ECG electrodes attached to the chest 105 of the subject 100 for measuring an ECG signal. The electrode signals are provided to an additional vital sign processor 30*a* (or, alternatively, to the vital sign processor 30) where the electrode signals are evaluated to obtain the ECG signal as additional vital sign which is also provided to the alarm unit 60.

Each of said additional sensors 10*a*, 10*b* is provided with a respective marker 20*a*, 20*b*, which may be active or passive markers as described above. The markers 21*a*, 21*b* are also monitored by the imaging unit 40 to detect their motion and, thus, motion of the sensors 10*a*, 10*b*. Thus, for each individual sensor 10, 10*a*, 10*b* it can be judged how reliable the signal measured by the respective sensor is. Further, by jointly analyzing the detected locations of the several sensors belonging to a particular subject 100, it is possible to recognize the situations when a particular sensor got detached (fell off) from the subject, a sensor was not attached to the sensor (e.g. if the sensor is not in the field of view of the imaging unit 40, or it is too far away from the other sensors of that subject), or the sensor got mistakenly attached to a different/wrong subject. If such a case is detected an appropriate alarm can be generated and outputted.

It should be noted that, particularly in an ICU setting, the sensors are generally exposed, i.e., they are not covered by blankets or the like, but that they are in the field of view of the imaging unit which e.g. is mounted on the ceiling. In the event that the marker is covered by a blanket and cannot be detected in the image data no localization information can be retrieved. This information (i.e., "sensor is invisible") can still be transmitted to the alarm unit 60, which then can operate in the conventional mode. However, during all other times, i.e., when the sensor and its marker is visible, information on sensor motion is available and can be used to reduce false alarms.

Figure 4:
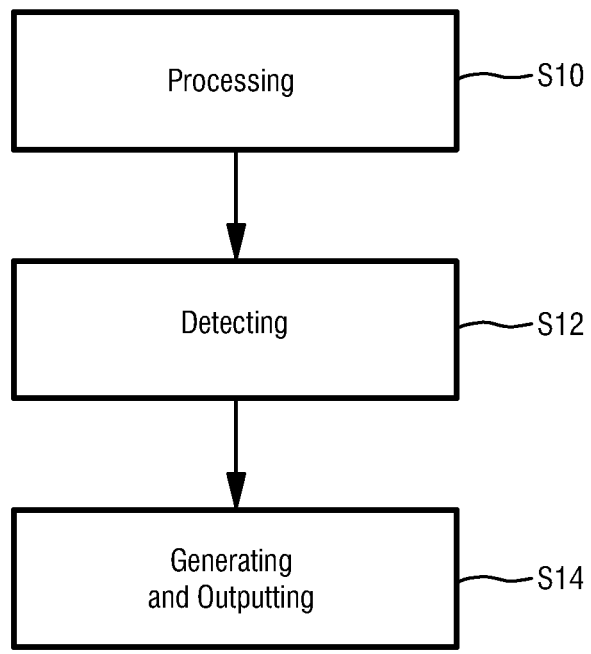
FIG. 4 shows a flow chart of a method for determining a vital sign of a subject.

FIG. 4 shows a flow chart of a method for determining a vital sign of a subject. In a first step S10 a measured vital sign information signal of said subject is processed to obtain a vital sign of said subject. In a second step S12 motion of a marker attached to said sensor is detected from image data image data obtained from at least an imaging region containing said sensor. Finally, in a third step S14 an alarm signal is generated and outputted based on the measured vital sign information signal and/or obtained vital sign and on the detected motion of said marker.

These steps of the method may be carried out by a single processor or computer (e.g. running a corresponding algorithm), or by several separate processors or computers, or by a dedicated hardware designed for this purpose.

In the following an exemplary scenario shall be described. A sleeping ICU patient lying in bed with his hands/arms on top of the blanket shall be considered. The patient has a fingerclip sensor equipped with a marker attached to one of his fingers to facilitate continuous heart rate (HR) monitoring. When such a sensor moves, e.g., due to patient movements, the HR measurement (referred to as HR signal in the following) is quite unreliable because of signal artifacts. During such movements the (falsely) derived HR can be outside the acceptable bounds.

From time to time the patient adjusts his position in bed and moves his hand during the process. This can take many seconds. The HR signal continues to contain artifacts during the movements. The derived HR is continuously high (say 200 BPM) due to false peak detections in the HR signal. This is outside the acceptable HR range, and an alarm should be generated. According to the present invention, however, the fast sensor motion is simultaneously detected in a video data stream monitoring the patient. The alarm unit (e.g. a processor executing a computer program for causing the processor to carry out the steps of the proposed method) decides, however, not to generate the alarm because both the HR is out of bounds and the sensor is moving, i.e. a false alarm is prevented.

Once, the patient movement is over the patient condition deteriorates and the HR really increases beyond safe levels. In this situation no sensor motion is detected in the video data stream. The HR estimate is determined to be reliable. Then, because the HR is too high and the sensor is not moving an alarm is correctly generated and outputted.

A similar scenario applies to non-invasive blood pressure measurements (NIBP) with a cuff equipped with a marker, where the measurement is only reliable when the patient does not move. An ICU patient in bed shall be considered again. An NIBP measurement is triggered by the system. If the patient moves during the process, the sensor/marker will move. If the movement intensity is beyond a certain threshold the unreliable NIBP measurement results will be discarded and no alarm will be raised. Instead, another measurement can be initiated shortly afterwards.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A system for determining a vital sign of a subject comprising:
   a sensor configured to be attached to a subject and generate a vital sign information signal indicative of a vital sign of the subject,
   a vital sign processor configured to process a vital sign from the vital sign information signal,
   an image analysis processor configured to detect motion of a marker attached to said sensor from image data obtained by a camera, and an alarm processor configured to generate and output an alarm signal in response to:
the vital sign fulfilling a first condition and,
the detected motion of said marker fulfilling a second condition.

2. The system as claimed in claim 1,
wherein said alarm processor is configured to use as the first condition at least one of a lower and an upper threshold of a level of the vital sign.

3. The system as claimed in claim 1,
wherein said alarm processor is configured to use as the second condition a motion threshold indicating the intensity, frequency and/or pattern of the motion of said marker.

4. The system as claimed in claim 1,
wherein said alarm processor comprises a communication interface for communicating said alarm signal to an alarm device for indicating an alarm.

5. The system as claimed in claim 1, wherein the marker is one of a passive marker comprising a graphical pattern and an active marker configured to emit light.

6. The system as claimed in claim 5,
wherein said marker is a passive marker comprising a graphical pattern, wherein said graphical pattern is configured to contain information about the subject and/or the sensor and wherein said image analysis processor is configured to determine said information about the subject and/or the sensor from said graphical pattern.

7. The system as claimed in claim 5,
wherein said marker is an active marker configured to emit light, wherein said active marker is configured to emit light containing information about the subject and/or the sensor and wherein said image analysis processor is configured to determine said information about the subject and/or the sensor from said emitted light.

8. The system as claimed in claim 5,
wherein said image analysis processor is configured to detect a location of said marker and one or more additional markers attached to one or more further sensors and/or to the subject's body from said image data; and
wherein said alarm processor is configured to generate and output the alarm signal in response to detecting that one of the sensors is not attached or is attached incorrectly or to a wrong portion of the subject's body or is attached to a wrong subject.

9. The system as claimed in claim 5,
wherein said alarm processor is configured to generate and output an alarm signal if the marker cannot be detected in said imaging region.

10. A system for determining a vital sign of a subject comprising:
a plethysmographic sensor attachable to the subject and comprising a light source that emits light in a first direction onto skin covered by said sensor, and in a second direction away from the skin,
an imaging unit configured to detect the light from the light source emitted in the second direction away from the skin,
a vital sign processor configured to process a vital sign information signal measured by the plethysmographic sensor to obtain a vital sign of said subject,
an image analysis unit configured to detect motion of said plethysmographic sensor from image data obtained by the imaging unit, and an alarm unit configured to generate and output an alarm signal based on the measured vital sign information signal and/or the vital sign processed from the measured vital sign information signal and on the detected motion of said plethysmographic sensor.

11. The system as claimed in claim 10,
wherein said alarm unit is configured to generate and output the alarm signal in response to the measured vital sign information signal and/or the vital sign fulfilling a first condition, wherein said first condition is adapted based on the detected motion of said sensor.

12. The system as claimed in claim 10,
wherein said alarm unit is configured to generate the alarm signal in response to the measured vital sign information signal and/or the vital sign fulfilling a first condition, wherein the output of said alarm signal is suppressed if the detected motion of said sensor fulfills a second condition.

13. The system as claimed in claim 10, further including a sensor housing that carries the light source, at least a part of the sensor housing being made from a translucent material such that the light emitted in at least the second direction passes therethrough.

14. A plethysmographic sensor comprising:
one light source configured to emit light;
a sensor housing designed such that the light emitted from the one light source is emitted out of the housing in a first direction and in a second direction away from the first direction, light emitted in the second direction being transmitted to a motion detector displaced from the plethysmographic sensor;
a light detector configured to receive the light emitted in the first direction after intersection with a patient, the light detector being mounted to the housing.

15. A system for determining a vital sign of a subject comprising:
a plethysmographic sensor configured to generate a vital sign information signal, the sensor comprising a light source configured to emit light in a first direction toward a subject and a light detector configured to receives the light transmitted in the first direction after interaction with the subject and generate the vital sign information signal, wherein said plethysmographic sensor is designed such that light from the light source is also emitted in a second direction away from the subject,
an imager configured to detect the light emitted in the second direction and generate image data,
at least one processor configured to:
process said vital sign information signal from said plethysmographic sensor to obtain a vital sign,
determine motion of said plethysmographic sensor from the image data generated by the imager, and
generate and output an alarm signal based on a combination of (1) the measured vital sign information signal and/or the obtained vital sign and (2) the determined motion of said plethysmographic sensor.

16. The system as claimed in claim 15,
wherein the at least one processor is further configured to generate and output the alarm signal in response to the vital sign information signal and/or the vital sign fulfilling a first condition, wherein said first condition is adapted based on the detected motion of said plethysmographic sensor.

17. The system as claimed in claim 15,
wherein the at least one processor is further configured to generate an alarm signal if the vital sign information signal and/or the vital sign fulfills a first condition, wherein the output of said alarm signal is suppressed if the detected motion of said marker fulfills a second condition.

18. A system for determining a vital sign of a subject, the system comprising:
a plethysmographic sensor configured to be worn by the subject, the plethysmographic sensor including:
a light source configured to emit light in at least a first direction and a second direction, the second direction being different from the first direction,
a light detector configured to receive the light emitted in the first direction and generate a detector signal indicative of the received light;
an imager configured to detect the light emitted by the light source in the second direction and generate image data;
at least one processor configured to:
determine physiological information from the detector signal;
determine motion of the plethysmographic sensor from the image data;
generate and output an alarm based on a combination of the physiological information and the plethysmographic motion.

19. The system as claimed in claim 18, wherein the first direction is toward the subject and further including a housing, the light source and the light detector being supported by the housing such that the light emitted in the first direction interacts with the subject before being detected by the light detector.

20. The system as claimed in claim 19, wherein the light source and the imager are disposed relative to each other such that the light in the second direction is detected directly by the imager without interacting with the subject.

* * * * *